US009592353B2

(12) United States Patent
Roy

(10) Patent No.: US 9,592,353 B2
(45) Date of Patent: Mar. 14, 2017

(54) ADAPTOR/TUBING WITH ALARM(S)

(71) Applicant: Sanjay K Roy, Palmetto Bay, FL (US)

(72) Inventor: Sanjay K Roy, Palmetto Bay, FL (US)

(*) Notice: Subject to any disclaimer, the term of this patent is extended or adjusted under 35 U.S.C. 154(b) by 0 days.

(21) Appl. No.: 15/140,135

(22) Filed: Apr. 27, 2016

(65) Prior Publication Data

US 2016/0317763 A1 Nov. 3, 2016

Related U.S. Application Data

(60) Provisional application No. 62/154,948, filed on Apr. 30, 2015, provisional application No. 62/203,060, filed on Aug. 10, 2015.

(51) Int. Cl.
*A61M 39/10* (2006.01)
*A61M 5/50* (2006.01)

(52) U.S. Cl.
CPC .......... *A61M 5/5086* (2013.01); *A61M 39/10* (2013.01); *A61M 2205/18* (2013.01); *A61M 2205/332* (2013.01); *A61M 2205/583* (2013.01); *A61M 2205/6027* (2013.01)

(58) Field of Classification Search
CPC .................. A61M 39/12; A61M 39/10; A61M 2039/1005; A61M 2205/332; A61M 2205/583; A61M 2205/6027
USPC ......................................... 439/489, 490, 190
See application file for complete search history.

(56) References Cited

U.S. PATENT DOCUMENTS

| | | | | |
|---|---|---|---|---|
| 3,595,228 A * | 7/1971 | Simon | ............... | A61M 16/0051 128/202.22 |
| 4,146,028 A * | 3/1979 | LeFevre | ............ | A61M 5/16831 138/30 |
| 4,294,250 A * | 10/1981 | Dennehey | ............. | A61M 39/10 604/403 |
| 4,316,182 A * | 2/1982 | Hodgson | ............... | A61B 5/0816 128/202.22 |
| 4,369,781 A * | 1/1983 | Gilson | .................. | A61M 5/346 285/332 |
| 4,446,869 A * | 5/1984 | Knodle | .................. | A61B 5/097 128/205.12 |
| 4,834,706 A * | 5/1989 | Beck | .................. | A61M 39/1011 604/111 |
| 5,071,413 A * | 12/1991 | Utterberg | ............... | A61M 5/162 604/411 |
| 5,263,945 A * | 11/1993 | Byrnes | .................. | A61M 39/12 285/238 |
| 5,312,377 A | 5/1994 | Dalton | | |
| 5,320,092 A * | 6/1994 | Ryder | ............... | A61M 16/0666 128/202.22 |

(Continued)

OTHER PUBLICATIONS

International Organization for Standardization: ISO 80369—Small-bore connectors for liquids and gases in healthcare applications (Multiple parts).

(Continued)

*Primary Examiner* — Abdullah Riyami
*Assistant Examiner* — Vladimir Imas

(57) ABSTRACT

The present invention relates to connectors for uses where an indicator/alarm must be activated if the axial force rises above a predetermined value. It can be used in applications where excessive forces on tubings/connectors are not acceptable, for example, in tubes/couplings in fluids, and in electronic/electric, optical and other systems where a strain-relief cannot be employed.

20 Claims, 3 Drawing Sheets

Schematic diagram of connector adaptor (section, unstressed)

(56) References Cited

U.S. PATENT DOCUMENTS

| | | | | |
|---|---|---|---|---|
| 5,385,372 A * | 1/1995 | Utterberg | A61M 39/20 | 215/306 |
| 5,620,427 A * | 4/1997 | Werschmidt | A61M 39/10 | 137/516.13 |
| 5,651,776 A * | 7/1997 | Appling | A61M 39/10 | 285/332 |
| 5,707,086 A * | 1/1998 | Treu | A61L 2/04 | 285/316 |
| 5,772,643 A * | 6/1998 | Howell | A61M 25/0014 | 138/155 |
| 5,954,313 A * | 9/1999 | Ryan | A61J 1/2096 | 251/149.1 |
| 6,027,482 A * | 2/2000 | Imbert | A61M 5/3134 | 604/240 |
| 6,217,560 B1 | 4/2001 | Ritger | | |
| 6,245,055 B1 * | 6/2001 | Fulford | A61M 25/0014 | 604/533 |
| 6,280,418 B1 * | 8/2001 | Reinhard | A61M 5/28 | 604/181 |
| 6,428,515 B1 * | 8/2002 | Bierman | A61M 25/02 | 128/DIG. 26 |
| 6,437,316 B1 * | 8/2002 | Colman | A61M 39/10 | 250/222.1 |
| 6,969,375 B2 * | 11/2005 | Thibault | A61M 5/344 | 604/241 |
| 7,059,322 B2 * | 6/2006 | Rich | A61M 16/0463 | 128/200.24 |
| 7,488,229 B2 * | 2/2009 | Ben-Oren | A61B 5/083 | 313/573 |
| 7,500,483 B2 * | 3/2009 | Colman | A61M 16/08 | 128/204.18 |
| 7,615,041 B2 * | 11/2009 | Sullivan | A61J 1/2096 | 604/403 |
| 7,727,194 B2 * | 6/2010 | Nalagatla | A61B 5/0836 | 604/122 |
| 7,758,562 B2 * | 7/2010 | Gelfand | A61B 5/201 | 604/31 |
| 7,799,065 B2 * | 9/2010 | Pappas | A61F 2/966 | 606/108 |
| 8,052,642 B2 * | 11/2011 | Harr | A61M 5/14232 | 600/310 |
| 8,192,421 B2 | 6/2012 | Lopez | | |
| 8,257,338 B2 * | 9/2012 | Keenan | A61K 49/223 | 424/9.52 |
| 8,257,663 B2 * | 9/2012 | Crawford | A61M 39/045 | 116/200 |
| 8,414,560 B2 | 4/2013 | Bush, Jr. | | |
| 8,545,479 B2 | 10/2013 | Kitani | | |
| 8,684,979 B2 * | 4/2014 | Deighan | A61M 39/10 | 285/332.1 |
| 8,746,745 B2 * | 6/2014 | Colman | A61M 39/1011 | 285/390 |
| 8,998,266 B2 | 4/2015 | Colman | | |
| 9,017,291 B2 * | 4/2015 | Delabie | A61M 5/344 | 604/187 |
| 9,149,623 B1 * | 10/2015 | Colman | F16L 25/01 | |
| 9,155,866 B2 * | 10/2015 | Bornhoft | A61M 25/02 | |
| 9,314,606 B2 * | 4/2016 | Colman | A61M 39/10 | |
| 9,387,316 B2 * | 7/2016 | Colman | F16L 25/01 | |
| 2006/0033334 A1 * | 2/2006 | Weber | A61M 39/10 | 285/390 |
| 2012/0169044 A1 * | 7/2012 | Kendrick | A61M 16/0816 | 285/313 |
| 2012/0323208 A1 * | 12/2012 | Bochenko | A61J 1/2096 | 604/404 |
| 2016/0230914 A1 * | 8/2016 | Roy | A61M 39/00 | |

OTHER PUBLICATIONS

International Organization for Standardization: ISO 594-1:1986—Conical fittings with a 6 % (Luer) taper for syringes, needles and certain other medical equipment—Part 1: General requirements.
International Organization for Standardization: ISO 594-2:1998—Conical fittings with 6 % (Luer) taper for syringes, needles and certain other medical equipment—Part 2: Lock fittings.

* cited by examiner

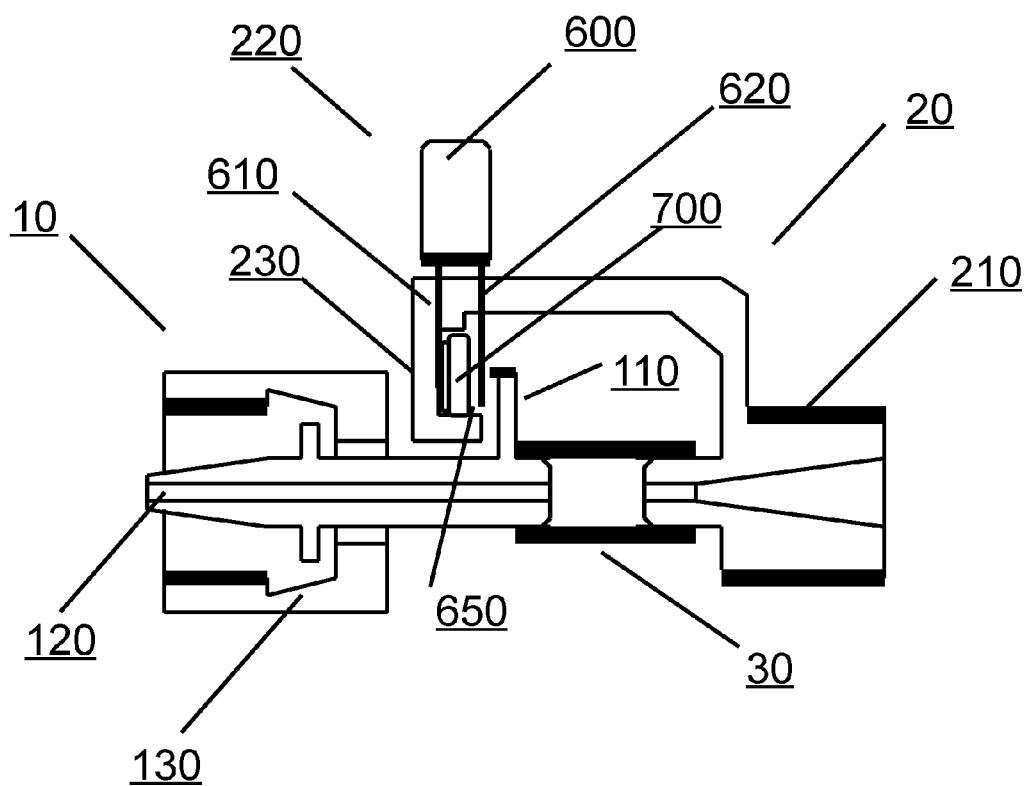
Fig.1 Schematic diagram of connector adaptor (section, unstressed)

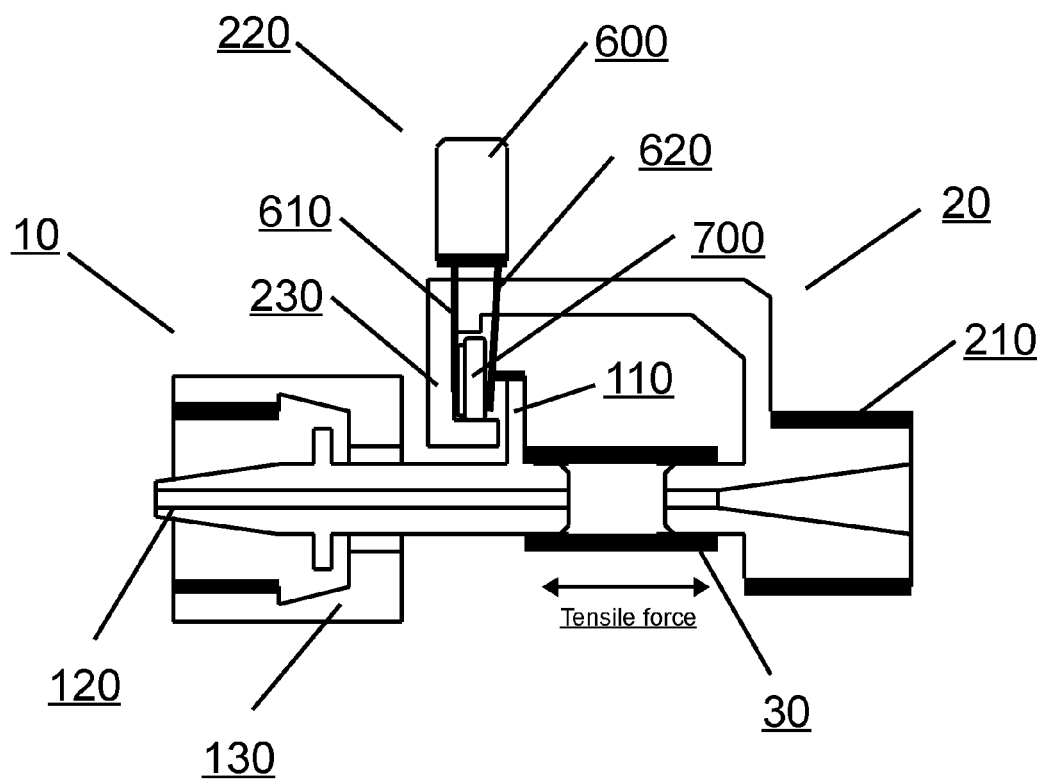
Fig. 2 Schematic diagram of connector adaptor
(section, under tensile load)

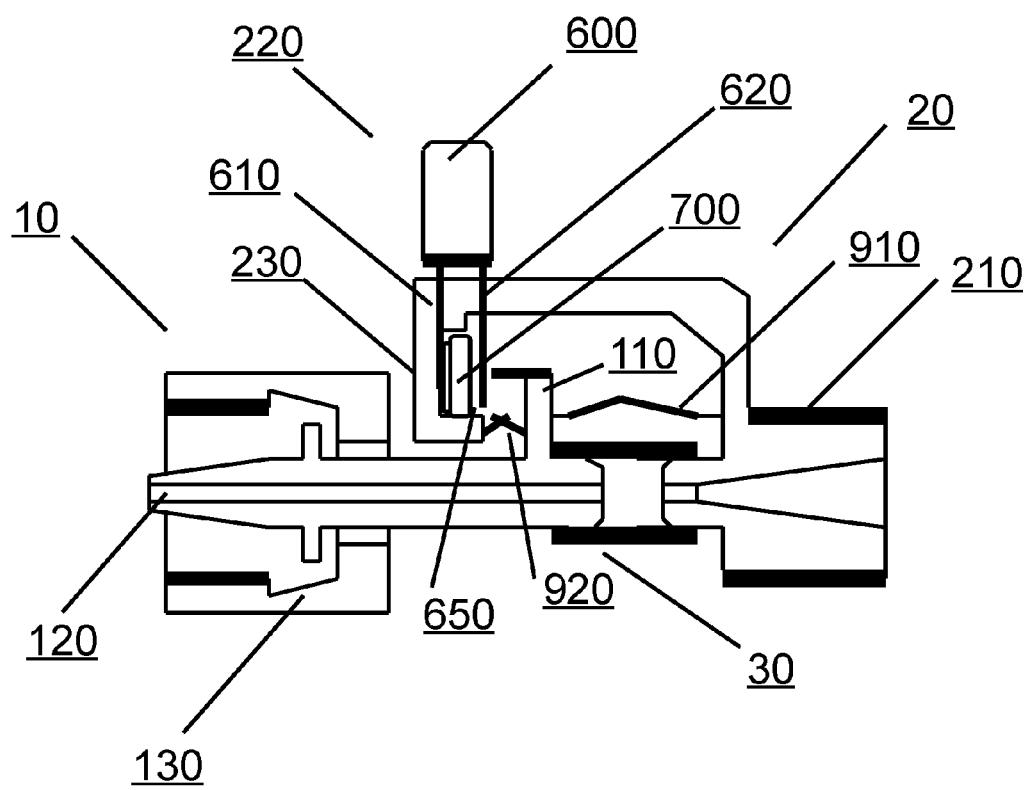
Fig.3 Schematic diagram of connector adaptor
- modified to include springs

ADAPTOR/TUBING WITH ALARM(S)

RELATED APPLICATIONS

This application claims the benefit of U.S. Provisional Application Ser. No. 62/154,948 filed on Apr. 30, 2015, and U.S. Provisional Application Ser. No. 62/203,060 filed on Aug. 10, 2015—the contents of which are incorporated by reference herein.

FIELD OF INVENTION

The present invention relates to luer connectors that are widely used in biomedical applications for coupling two tubings employed for carrying various types of fluids. It is specifically designed for uses where an indicator/alarm must be activated if the axial force on the two luer-lock connected tubes rises above a predetermined value. It can also be used in other applications where excessive forces on tubings/connectors are not acceptable, for example, in tubes/couplings in fluids, and in electronic/electric, optical and other systems where a strain-relief cannot be employed.

BACKGROUND OF THE INVENTION

Luer lock connectors are used in many biomedical systems to couple two fluid carrying tubes. A major advantage of these connectors is their lockable coupling-decoupling feature that can be easily manipulated by a single user. The connectors themselves comprise standardized mating conical coupling surfaces (e.g. ISO 594, 80369) designed to prevent leaks under normal operating pressures, which are relatively low (typically below 300 kPa). The locking feature comprises a double start right handed female threaded nut on one connector that locks on to a corresponding male thread or lug feature on the other connector.

Unfortunately, luer-lock (and other locking) connectors often cause significant problems when the axial forces are excessive. An example of this is associated with the use of catheters for collecting a fluid in a bag for future disposal. Since the collection bag may need to be replaced well before the catheter itself, a typical arrangement comprises a catheter-tubing assembly and a collection bag-tubing assembly that are coupled together using luer-lock connectors. In this situation, a significant axial/pulling force on the overall assembly can occur if the tubing gets caught or tangled up accidentally in clothing, limbs, bedding, or other similar objects. This can result in the catheter being pulled out of the body causing injury and harm to the patient.

DESCRIPTION OF THE PRIOR ART

One solution to the above is to use luer slip connectors instead of lock connectors. However, with this approach, the fluid begins to leak if the connectors disengage due to excessive forces. When this occurs, the user/patient is often not aware of this for a period of time, and extensive cleanup may be required when the disengagement is finally noted. Another alternative that is often used in various engineering applications, is to implement a "strain-relief" feature at the coupling that transmits the axial force to a rigid member that can absorb the high forces (e.g. a chassis). Unfortunately, this approach is not feasible when the coupling is being used with a human body.

Given the above, it is clear that there is a need for a adaptor that can be used with a luer-lock connector assembly that will activate an alarm when the axial pulling forces become excessive (i.e. rises above a predetermined/maximum value). It is also very important that the overall connector-adaptor-alarm assembly be simple, compact and low cost, so that it can be disposable, thereby permitting its use in biomedical applications. Similar low cost connector-alarm assemblies can also be used in other fluid, electrical and optical systems where it is often impractical, inefficient or expensive to incorporate strain reliefs in large networks.

SUMMARY OF THE INVENTION

The object of this invention is to provide a connector adaptor assembly that overcomes the disadvantages of current luer-lock connectors as mentioned above. The invention achieves this by combining the following:
- a luer-lock connector adaptor that provides the basic connection between the two fluid lines,
- a battery powered, low cost alarm assembly, and
- an integrated triggering mechanism that activates the alarm when the axial forces become excessive during use.

For catheter type applications described above, it is expected that the maximum force requirement will be of the order of 300-400 grams or lower. For other applications, it may be different.

BRIEF DESCRIPTION OF THE DRAWINGS

FIG. 1 is a schematic sectional diagram of a preferred embodiment of the invention in an unstressed condition.

FIG. 2 is a diagram showing the connector when it switches on under a tensile stress.

FIG. 3 is a schematic diagram of the preferred embodiment that has been modified to include springs.

DETAILED DESCRIPTION

FIG. 1 is a schematic view of a preferred embodiment of the present invention. It consists of the three sections, a male side connector section (10), a female side connector subassembly (20) and an elastic member (30), that together form the overall assembly.

The male side connector section (10) comprises a switching plate (110) and a standard luer-lock (male) connector (120) with a locking nut (130). The female side connector (20) comprises a standard luer-lock (female) connector (210), an alarm (220) and a stop feature (230). The elastic member (30) comprises a bellows or a tube section made of an elastomeric material, and connects the male side connector section (10) and the female side connector assembly (20) in a leak-proof manner.

The alarm (220) itself comprises only two components, an LED indicator module (600) and a battery (700). A through-hole mount LED module (600) is the primary component in the preferred embodiment. This module (600) is selected such that its forward voltage corresponding to the preferred output light intensity matches the output of the second component, the battery (e.g. 3 V for common Li cells).

The alarm (220) is integrated (or mounted in) the stop feature (230) such that:
- one of the (i.e. either the positive or the negative) leads (610) of the LED module (600) in direct electrical contact with corresponding terminal of the battery (700), and
- the other lead (620) is positioned adjacent to the second terminal with a gap (650) between them so that there is no electrical contact.

In its normal (i.e. unstressed) configuration shown in FIG. 1, the switching plate is in the far position, thereby ensuring that the alarm (220) is turned off since its electrical circuit is open due to the gap (650) between the second lead (620) and the battery terminal. When the connector adaptor is under axial tensile stress (see FIG. 2), the elastic member (30) elongates, thereby pulling the switching plate (110) towards the stop feature (230). When the axial force is high enough, the switching plate (110) makes contact with the alarm/stop (220/230), the second lead (620) comes in direct contact with the battery terminal and the alarm (220) turns on. When the axial force reduces, the reverse action occurs, and the alarm (220) switches off.

It is important to note that the cost and size of the device will be very low. This is due to the following unique features of the invention:

Electrical switching is achieved by using the lead of a component itself. All contacts can be done mechanically by enforcing using suitable tolerances in the male side connector section and the female side connector subassembly design.

The alarm actuation force in this configuration is determined by tensile force-extension characteristics of the elastic member. Proper functioning of the device can be obtained directly by using polymer bellows or elastic tubes (e.g. latex, rubber, etc.) of different wall thicknesses/geometries as required.

Only two electrical components are used, and individual components such as PCBs, electromechanical switches, battery holders and other electronic parts not required in the preferred embodiment. Hence, cost adders related to PCB assembly and packaging are eliminated. Also, strain gages (or force transducers) are not used for sensing the applied force: this conventional approach would be far more expensive due to the additional costs of integrating the sensors with the coupling and the costs of the additional electronics.

The present invention is not limited to the above described embodiments, and different variations and modifications that may be evident to one skilled in the art are possible without departing from its overall scope. For example, specific features that will enhance manufacturability of the connector components can and will be incorporated into the above embodiments to ensure that it can be manufactured at a reasonable cost (e.g drafts on other surfaces, rounds, etc.). Other variations of the above configuration include the following:

a. The second lead can be mounted directly on the switching plate. This will ensure that it cannot come in contact with the second battery contact inadvertently during use when there is no/little axial pulling force. In this approach, the switching plate can be made of an electrically conductive material to simplify the design/manufacturability.

b. The positions of the switching plate and the stop feature with the alarm can be interchanged between the male side connector section and the female side subassembly (i.e. the switching plate and the stop are effectively interchangeable). It is only necessary that the switching plate be in a position to activate the alarm when the elastic member is stretched.

c. An additional guide feature can be used to ensure that the stop/alarm and switching plate remain properly oriented with each even in the presence twisting or other motions. Such a design will be more robust.

d. In general, it is not essential that the match between the LED module and battery is perfect: it is only necessary that the battery voltage be higher than the LED forward voltage for the minimum required luminosity. However, if necessary, a resistor can be added to the electrical circuit (i.e. at the LED lead or battery) to ensure better match between the LED module and the battery, thereby improving the device life and reliability.

e. Battery contacts or other other extensions may be attached to the leads of the LED module (e.g. via crimping, spot welding, soldering, etc.) to improve the electrical contact between the LED and the battery if necessary. This may be appropriate if the length of the LED leads are too small. Alternatively, contact pins or receptacles (possibly with battery holders) may be integrated with the battery itself, if the resulting higher costs are acceptable.

f. The elastic member can have many different configurations. For example, a helical tubing (or other coil, formed or flexible tubing) can provide the required elastic function. Another option is to use spring(s) in combination with a flexible tube. In this case, the force associated with the device operation will be result from a combination of the spring force and the force on the tube. In an extreme case, the device can be designed so that the force from the tube is very low/negligible, and the elastic force required is provided primarily by the spring itself. Note that separate springs are not necessary: a low cost method would be to integrate a mechanical feature(s) that functions as a spring with the male side connector section and/or the female side connector subassembly Two simple approaches here are as follows (see FIG. 3; other methods are clearly possible):

(i) A tension spring (910) can be used together with (in parallel) with a flexible tube.

(ii) A compression spring (920) can be placed between the stop and the switching plate (instead of, or in addition to, the tension spring).

g. Instead of an LED module, other transducers or alarm modules may be used in this invention. Some alternatives include electromagnetic or piezoelectric buzzers, other light emitting devices, vibratory motors or even low power RF transmitters, etc. Note that the power source (i.e. the battery) may be need to be changed so as to match the transducer requirement. The overall construction however will be similar to the one described above.

h. More than one alarm can be used if necessary. For example, the assembly can comprise an LED as well as an audio buzzer with an integrated drive circuitry. This can be useful if the adaptor is used together with many other connectors/adaptors in a location that is not always visible. The audio alarm can then provide the initial indication for a supervisor at a distance: the specific alarm that has been activated can be identified more readily (amongst many) using the LED on closer inspection. Different configurations are feasible here, e.g.:

(i) Both the LED and the buzzer can be mounted around a single battery and activated at the same time (as is done for the single alarm design).

(ii) Two (or more) separately powered alarm modules can be integrated with the adaptor—the design of each of the alarm modules can be similar to the LED based alarm described above.

i. More complex versions may use PCB based designs with light (or other) transducers and specially designed drive circuits to allow for more flexibility in use and application. Rechargeable batteries with charging circuits, electromechanical switches, etc. are additional options that can be considered, through these can be expected to increase cost and size.

j. Other complex versions may use the switching plate to activate/deactivate a board mounted electromechanical or proximity switch instead of contacting the electrical lead in the alarm module. More precise switching can be obtained using magnetic technology, e.g. using permanent magnet(s) or using hall sensor switches.

k. Different versions of the overall connector adaptor assembly can be made with different fittings (e.g. hose, tube, pipe, etc.) at the open ends to accommodate corresponding fittings for different applications. Note that it is not necessary to use a "female" and "male" connector in a general case—any two connectors can be used at the two ends as long as they correspond to the connectors used in an existing circuit. For biomedical applications as proposed, luer lock fittings are incorporated on the two open ends so that the overall connector assembly can used together with existing luer lock connectors.

Finally, it is also important to note the following:

(i) The adaptor assembly described above can be directly implemented on existing elastic hoses/tubings of catheters and other equipment. In this approach, the invention will comprise a stop feature and a corresponding alarm feature that are mounted on the existing tubing with appropriate clamping features. By positioning them at carefully selected locations (depending on the required actuating force), the alarm can be made to turn on when the tube is stretched by an applied tensile force.

(ii) The above configurations are also suitable for electrical, optical, mechanical and other similar connectors and connector assemblies. In these applications, the tubing can be replaced by a a cable/cable assembly (a coiled or other formed cable for example) and spring combinations as described in (f) above to provide the elastic force. The overall design will otherwise be similar.

What is claimed is:

1. A luer-lock connector adaptor for fluid transfer comprising a luer-lock connector section, a slip connector subassembly, and an elastic member,
    said luer-lock connector section comprising a first luer-lock connector, a locking nut and a switching plate,
    said slip connector subassembly comprising a second luer-lock connector and a stop feature with an integrated alarm,
    said alarm comprising an alarm module and a battery,
    said alarm module comprising an LED indicator with two external connector leads, one positive and one negative,
    said battery providing electric voltage and power to drive said alarm module,
    said alarm module and battery positioned with
    one of positive or negative lead of alarm module in electrical connection with corresponding terminal of said battery and
    the other of said positive or negative lead of said alarm module adjacent to other corresponding terminal of said battery but not in electrical connection with it when there is no tensile force applied to
    said luer-lock connector adaptor,
    said elastic member connecting said luer-lock connector section and said slip luer-lock connector subassembly to allow fluid transfer between the two in a leak-proof manner, and
    said elastic member extending when an external tensile force is applied to said luer-lock connector adaptor, thereby moving said switching plate and said other lead of said alarm module towards said battery such that it makes electrical connection with said other corresponding terminal of said battery.

2. The luer-lock connector adaptor of claim 1, wherein a battery contact is attached to at least one of said leads of said alarm module and said battery contact is used to make electrical contact with corresponding contact of said battery.

3. The luer-lock connector adaptor of claim 1, wherein other of said positive or negative lead of alarm module is attached to said switching plate.

4. The luer-lock connector adaptor of claim 3, wherein said switching plate is made of an electrically conductive material.

5. The luer-lock connector adaptor of claim 1, wherein said elastic member comprises an elastomeric tube or a bellows element or a coiled tube.

6. The luer-lock connector adaptor of claim 5, wherein said elastic member comprises a tensile spring.

7. The luer-lock connector adaptor of claim 1, comprising a compression spring between said stop feature and said switching plate.

8. A luer-lock connector adaptor of claim 1, wherein said alarm module comprises a second transducer with integrated drive circuitry, with leads of said transducer connected electrically in parallel with leads of said LED indicator when said alarm is actuated.

9. A luer-lock connector adaptor of claim 1, wherein said alarm comprises multiple alarm modules with batteries.

10. A connector adaptor comprising a first connector section, a second connector subassembly, and an elastic member,
    said first connector section comprising a connector fitting and a switching plate,
    said second connector subassembly comprising a second connector fitting and a stop feature with an integrated alarm,
    said alarm comprising an alarm module and a battery,
    said alarm module comprising a a transducer integrated with any required drive circuitry, with two external connector leads, one positive and one negative,
    said battery providing electric voltage and power to drive said alarm module,
    said alarm module and battery positioned with
    one of positive or negative lead of said alarm module is in electrical connection with corresponding terminal of said battery and
    the other of said positive or negative lead of said alarm module adjacent to other corresponding terminal of said battery but not in electrical connection with it when there is no tensile force applied to
    said connector adaptor,
    said elastic member connecting said first connector section and said second connector subassembly to form a continuous path, and
    elastic member extending when an external tensile force is applied to said connector adaptor,
    thereby moving said switching plate and said other lead of said alarm module towards said battery such that it makes electrical connection with said other corresponding terminal of said battery.

11. The connector adaptor of claim 10, wherein a battery contact is attached to at least one of said leads of said alarm module and said battery contact is used to make electrical contact with corresponding contact of said battery.

12. The connector adaptor of claim 10, wherein other of said positive or negative lead of alarm module is attached to said switching plate.

13. The connector adaptor of claim 10, wherein said elastic member comprises an formed elastomeric member or a bellows element, or a coiled member.

14. The connector adaptor of claim 13, wherein said elastic member comprises a tensile spring.

15. The connector adaptor of claim 10, comprising a compression spring between said stop feature and said switching plate.

16. The connector adaptor of claim 10, wherein said alarm module is one of a piezoelectric buzzer, a electromagnetic buzzer, a LED module or an wireless transmitter module.

17. The connector adaptor of claim 10, wherein said connector fitting and said second connector fitting are of fluid, electrical or optical type.

18. A connector adaptor for one of fluid or data transmission, comprising a first connector section, a second connector subassembly, and an elastic member,
  said first connector section comprising a connector fitting and a switching plate,
  said second connector subassembly comprising a second connector fitting and an integrated alarm,
  said alarm comprising an alarm module, a battery and a switching means that are combined together in a continuous electrical circuit,
  said switching means having an on position wherein said electrical circuit is closed and an off position wherein said electrical circuit is open,
  said elastic member connecting said first connector section and said second connector subassembly to form a continuous path for said fluid or data transmission, and
  said switching means being in the off position when there is no tensile force applied to said connector adaptor, and said switching plate moving relative to said switching means to force it to its on position when an external tensile force is applied to said connector adaptor.

19. An apparatus using a connector adaptor for one of fluid or data transmission, comprising a first connector section, a second connector subassembly, and an elastic member,
  said first connector section comprising a connector fitting and a switching plate,
  said second connector subassembly comprising a second connector fitting and an integrated alarm,
  said alarm comprising an alarm module, a battery and a switching means that are combined together in a continuous electrical circuit,
  said switching means having an on position wherein said electrical circuit is closed and an off position wherein said electrical circuit is open,
  said elastic member connecting said first connector section and said second connector subassembly to form a continuous path for said fluid or data transmission, and
  said switching means being in the off position when there is no tensile force applied to said connector adaptor, and said switching plate moving relative to said switching means to force it to its on position when an external tensile force is applied to said connector adaptor.

20. An apparatus for one of fluid or data transmission comprising an elastic member, a switching plate and an alarm,
  said elastic member providing a continuous path for said fluid or data transmission,
  said switching plate and alarm being mounted on said elastic member,
  said alarm comprising an alarm module, a battery and a switching means that are combined together in a continuous electrical circuit,
  said switching means having an on position wherein said electrical circuit is closed and an off position wherein said electrical circuit is open, and
  said switching means being in the off position when there is no tensile force applied to said connector adaptor, and said switching plate moving relative to said switching means to force it to its on position when an external tensile force is applied to said elastic member.

* * * * *